(12) United States Patent
Harttig et al.

(10) Patent No.: US 8,586,376 B2
(45) Date of Patent: Nov. 19, 2013

(54) METHOD FOR PRODUCING AN ANALYSIS ELEMENT SPREADING LAYER

(75) Inventors: Herbert Harttig, Neustadt (DE); Bernd Hiller, Lampertheim (DE); Wolfgang Schwoebel, Mannheim (DE); Alexander Kasejew, Mannheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 13/332,076

(22) Filed: Dec. 20, 2011

(65) Prior Publication Data

US 2012/0189496 A1 Jul. 26, 2012

Related U.S. Application Data

(63) Continuation of application No. PCT/EP2010/003751, filed on Jun. 22, 2010.

(30) Foreign Application Priority Data

Jun. 24, 2009 (EP) .................................... 09008233

(51) Int. Cl.
*G01N 21/75* (2006.01)
(52) U.S. Cl.
USPC .......... 436/166; 422/68.1; 427/289; 427/290; 118/264; 83/870; 83/874
(58) Field of Classification Search
None
See application file for complete search history.

(56) References Cited

U.S. PATENT DOCUMENTS

| 3,802,842 | A | 4/1974 | Lange et al. |
| 4,624,665 | A * | 11/1986 | Nuwayser ..................... 604/307 |
| 5,846,837 | A | 12/1998 | Thym et al. |
| 6,110,369 | A | 8/2000 | Ditter et al. |
| 7,964,049 | B2 | 6/2011 | Kapur et al. |
| 2006/0292324 | A1* | 12/2006 | Roberts ...................... 428/36.91 |

FOREIGN PATENT DOCUMENTS

| DE | 213348 A1 | 1/1972 |
| DE | 102007035583 A1 | 4/2008 |
| EP | 1114997 A2 | 7/2001 |
| EP | 1640716 A1 | 3/2006 |
| GB | 1331775 | 9/1973 |
| WO | 98/25758 A1 | 6/1998 |
| WO | 03/097219 A1 | 11/2003 |

* cited by examiner

*Primary Examiner* — Lyle Alexander
(74) *Attorney, Agent, or Firm* — Harness, Dickey (57) ABSTRACT

Methods of producing an analysis spreading layer for absorbing a liquid to be analyzed, by: supplying a porous membrane having a bottom, a top and a thickness D, the size of the pores of the membrane increasing over its thickness D; cutting the membrane at a predefined distance, the spreading layer being a sublayer with a thickness d less than the starting thickness D, the pores of the spreading layer having a fluid connection to one another in such a manner that it is permeable to a liquid. The membrane surface is formed by removing a sublayer of the membrane being the liquid outlet side of the spreading layer. The mean size of the pores on the liquid outlet side is at least 1 μm.

16 Claims, 6 Drawing Sheets

METHOD FOR PRODUCING AN ANALYSIS ELEMENT SPREADING LAYER

CROSS-REFERENCE TO RELATED APPLICATIONS

This application is a continuation of International Application No. PCT/EP2010/003751, filed Jun. 22, 2010, which claims the benefit and priority of European Application No. 09008233.0, filed Jun. 24, 2009. The entire disclosures of the above applications are incorporated herein by reference.

BACKGROUND

The present invention relates to a method for producing an analysis element spreading layer, which is implemented for the purpose of absorbing a liquid to be analyzed, e.g., a body fluid, in a preferably optical analysis element and distributing it uniformly over a liquid outlet side of the spreading layer. The invention also relates to a spreading layer, which is a porous membrane. Such a spreading layer can be part of an analysis element, which is primarily used for medical analyses. An important area of application of the invention is the assaying of very small sample volumes, which are typically obtained through a puncture in the skin of the patient. The body fluid sample quantities are preferably less than 1 µl.

The analysis is performed using a reagent system, which preferably comprises multiple reagents and auxiliary materials, which are integrated in the analysis element. The reaction of the reagents with an analyte contained in the body fluid results in a measured variable, which is characteristic for the desired analytical result and can be measured on the analysis element. The invention is especially oriented to so-called optical analysis systems and analysis elements, in which the characteristic change of the analysis element, which is a measure of the quantity and/or the presence of an analyte, is optically measurable. The reaction of the body fluid in the analysis element typically results in a change of the color in an analysis layer, which is part of the analysis element and is also designated as a detection layer. The color change of the detection layer is photometrically measured in the wavelength range from approximately 300 nm to approximately 1400 nm. In addition to colorimetric systems, other systems which can be optically evaluated are also known, for example, systems based on fluorescence measurements.

Analysis systems in numerous variants are typical for the qualitative and quantitative determination of various analytes. Systems for determining the glucose concentration in the blood of diabetics have particularly great significance. The invention is particularly suitable for such systems, but it is not restricted thereto. Such systems are performed by the patient himself, for example, for monitoring the health status of the patient ("home monitoring"). Therefore, they must be simple to operate, as small as possible, and robust. Since multiple measurements and therefore also multiple punctures in the skin must be performed daily for a reliable observation of the health status, the quantity of blood removed is to be as small as possible, so that it can also be performed with low puncture depths and therefore with a low-pain puncture.

Optical analysis elements typically have a support structure, which comprises plastic and is often an oblong plastic strip ("test strip"). A so-called test layer, which comprises at least a part of the reagents and the detection layer, adjoins the support layer of the analysis element. The test layer can comprise one or more layers, which are in fluid contact with one another and typically run parallel to one another and to the support layer. Reagent-containing layers ("reagent layers") of the test layer often comprise an absorbent porous layer material, such as paper or nonwoven material, in which the reagents are impregnated.

In addition to the absorbent porous materials, there are also test layers in which at least one reagent layer is applied to a suitable transparent carrier material by coating. To produce such a coated test layer (CTL), which is designated as a reagent film, reagents mixed into a thickener are applied in the form of a more or less viscous coating compound as a thin film to the carrier material and dried. Upon contact of the reagent film with the aqueous sample liquid, the reactions with the reagents which are required for the analysis occur. For this purpose, the reagent film is typically absorbent and/or swellable and/or soluble. Such systems require a liquid retention structure, which is in fluid contact with the reagent film and uniformly distributes a liquid.

The precision of the analytical results in optical analysis systems and optical analysis elements is substantially dependent on the homogeneity of the coloration in the detection layer of the test layer. In order to reduce inhomogeneities, it is typical to provide a spreading layer adjacent to the test layer of the analysis element, since a uniform distribution of the sample liquid to be analyzed over the test layer is a requirement for a reliable and informative analysis. A liquid outlet side of the spreading layer, which faces toward the test layer, is in fluid contact with a liquid inlet side of the test layer. The spreading layer is implemented so that a liquid penetrating therein is uniformly distributed on its liquid outlet side. During the formation of the spreading layer, materials are used in which a rapid propagation of the body fluid sample occurs over the entire area of the layer. The propagation typically occurs through capillary activity of the spreading layer. Therefore, loose fiber composite structures are suitable, in particular fabrics, papers, or nonwoven materials made of hydrophilic or hydrophilized threads and fibers. Examples of such analysis elements are found in DE 2118455, Boehringer Mannheim GmbH, published Sep. 21, 1972 (see also, U.S. Pat. No. 3,802,842, Lange et al., issued Apr. 9, 1974) and DE 19629657, Boehringer Mannheim GmbH, published Jan. 29, 1998 (see also U.S. Pat. No. 5,846,837, Thym et al., issued Dec. 8, 1998).

In order to ensure reproducible color changes in the detection layer of the analysis element in optical analysis systems, a certain minimum height of a liquid layer having the analyte is necessary, which adjoins the detection layer of the analysis element. The liquid layer thickness is frequently between 50 µm and 200 µm, in particular in the case of enzymatic tests. It is ensured by the accordingly dimensioned spreading layers.

In the case of the processing of small sample volumes less than 1 µl, the known spreading structures have proven to be disadvantageous, however. Structures made of a fine fabric, which are knitted or woven by threads or fibers, have the disadvantage for very small test layers and test layer zones, whose lateral extension of the measuring spot in the test layer plane is in the range of 100 µm to 300 µm, that the mesh width is also in the range of 100 µm. This causes an inhomogeneous formation of the coloration based on the reaction in the detection layer, since the diffusion of analyte from the supernatant sample into the chemical layer is obstructed below a thread. If the threads are processed into a mesh fabric having smaller mesh widths, an excessively small free volume, in which liquid can be absorbed, results in comparison to the total volume of the spreading structure. In addition, the thickness of the thread is excessively large in comparison to the mesh width, so that an optical evaluation is no longer possible. The use of thinner threads is precluded because an adequate layer height in the spreading layer cannot thus be ensured.

Papers or nonwoven materials are also not suitable for the processing of small sample volumes, since they are fundamentally inhomogeneous and have a certain "cloudiness" in the case of optical measurement. The inhomogeneities thus caused in the coloration are negligible in large test layer zones and large optical evaluation areas through averaging. However, in small test layers having an extension of the measuring spot of less than 300 μm in the test layer plane, reliable optical evaluations may not be performed.

SUMMARY

The invention is based on the technical problem of producing an improved analysis element and an improved analysis element spreading layer, which particularly allow a very good measurement precision to be ensured with extremely small sample quantities in the case of an optical measuring method. In addition, the production of the spreading layer is to be cost-effective.

The technical problem is solved by a spreading layer which is produced from a porous membrane. According to the invention, methods are provided for producing an analysis element spreading layer, which is implemented for absorbing a liquid to be analyzed in an analysis element and distributing it uniformly over a liquid outlet side of the spreading layer, the method comprising supplying a porous starting membrane having a top side, a bottom side and a starting thickness D between the bottom side and the top side, the size of the pores of the starting membrane increasing at least sectionally over its starting thickness D; cutting the starting membrane at a predefined distance parallel to its top side in such a manner that a sublayer of the starting membrane is removed, wherein the spreading layer is a sublayer of the starting membrane, whose thickness d is less than the starting thickness D of the starting membrane, the pores of the spreading layer are a fluid connection to one another in such a manner that it is permeable to a liquid, the membrane surface formed by the removal of a sublayer of the starting membrane is the liquid outlet side of the spreading layer, and the mean pore size of the pores on the liquid outlet side of the spreading layer is at least 1 μm.

An optimized analysis element comprising a test element and an analysis element spreading layer is produced using a method, comprising supplying a porous starting membrane having a top side, a bottom side, and a starting thickness D between the bottom side and the top side, the size of the pores of the starting membrane at least sectionally increasing over its starting thickness D; removing a sublayer of the starting membrane at a predefined distance parallel to its top side in such a manner that the spreading layer is a sublayer of the starting membrane having a thickness d, which is less than the starting thickness D of the starting membrane, wherein the pores of the spreading layer are a fluid connection to one another in such a manner that they are permeable to a liquid, the membrane surface formed by the removal of a sublayer of the starting membrane is the liquid outlet side of the spreading layer, and the mean pore size of the pores on the liquid outlet side of the spreading layer is at least 1 μm; supplying the spreading layer formed to a test field having a support layer and a test layer, wherein the test layer comprising a reaction layer having at least one reagent, which is part of a reagent system for detecting an analyte in the liquid sample; applying the spreading layer to the moist test field in such a manner that the liquid outlet side of the spreading layer presses against a top side of the test layer, so that the spreading layer and the test field are connected and jointly form the analysis element.

A spreading layer and an analysis element are provided for absorbing a liquid to be analyzed and for uniformly distributing the liquid over a liquid outlet side, wherein the spreading layer is a porous membrane that has a top side opposite to the liquid outlet side, which forms a liquid inlet side. The spreading layer comprises a plurality of pores that are in fluid contact with one another in such a manner that the spreading layer is permeable to a liquid. The mean pore size increases along the thickness d of the spreading layer in such a manner that the mean pore size on the liquid inlet side is greater than the mean pore size on the liquid outlet side. The mean pore size on the liquid outlet side is at least 1 μm, preferably at least 2 μm, particularly preferably at least 5 μm and/or the mean pore size of the liquid outlet side is at most 20 μm, preferably at most 10 μm, particularly preferably at most 7 μm, and the free pore area on the liquid outlet side of the spreading layer is at least 70%, preferably at least 80%, particularly preferably at least 90%.

In another embodiment, analysis elements comprise a test field having a support layer and a test layer applied to the support layer, the test layer having a reaction layer with at least one reagent and the reagent being part of a reagent system for detecting an analyte in a liquid sample, and a spreading layer for absorbing a liquid sample and for uniformly distributing it over a liquid outlet side facing toward the test field, characterized in that the spreading layer is a porous membrane, which has a top side opposite to the liquid outlet side, which forms a liquid inlet side. The spreading layer comprises a plurality of pores, which are a fluid connection to one another in such a manner that the spreading layer is permeable to a liquid. The mean pore size increases along the thickness of the spreading layers in such a manner that the mean pore size on the liquid inlet side is greater than the mean pore size on the liquid outlet side. The mean pore size on the liquid outlet side is at least 1 μm, preferably at least 2 μm, particularly preferably at least 5 μm and/or the mean pore size of the liquid outlet side is at most 20 μm, preferably at most 10 μm, particularly preferably at most 7 μm; and the free pore area on the liquid outlet side of the spreading layer is at least 70%, preferably at least 80%, particularly preferably at least 90%; and the spreading layer is in contact with the test field in such a manner that the liquid outlet side presses against the test layer.

It has been established in the context of the invention that the spreading layer can be obtained from a porous membrane. However, the known, commercially available membranes do not meet all requirements for a spreading layer for detecting analytes in a liquid, preferably in a body fluid such as blood. In order to allow short analysis times, the absorption and the transport of the sample liquid must occur rapidly. This requires a hydrophilic surface of the pore structure, a suitable pore structure, and an appropriately dimensioned total thickness of the membrane.

Porous polymer membranes are typically hydrophobic. The external surfaces and the pore surfaces of the membrane are finished as hydrophilic by treatment with wetting agents and/or coatings and therefore become wettable for the sample. An intrinsic contact angle of <90° is fundamentally adequate, however, finishes having an intrinsic contact angle less than 70°, particularly preferably less than 60°, are preferred. The intrinsic contact angle is understood as the contact angle which is observed on an ideal smooth surface of the relevant material.

Considered over the thickness, the pore structures of various membranes differ substantially. In so-called symmetrical membranes, the pore size is equal on both outer sides of a membrane. In so-called asymmetrical membranes, the pore size is different on both sides. Particularly in the case of highly asymmetrical membranes, the pore sizes differ by more than one order of magnitude.

The surfaces of a membrane typically have a different distribution of the pore sizes than the layer located immediately underneath. This applies in particular to phase inversion membranes. The membrane side which faced toward the precipitant during the production process frequently has a skin-like surface therein. Such a surface is characterized in that the area which is formed by open pores is smaller in comparison to the area which is formed by the membrane material than in the case of corresponding areas in the interior of the membrane. The fraction of the area of the total geometrical area of a surface which is formed by open pores is designated hereafter as the "free pore area". The unit of this relative open area is percent.

Because of the increasing capillarity activity of smaller pores, liquid is preferentially absorbed by small pores. A capillary transport is preferentially performed from large pores to small pores. Thus, if a sample is delivered onto the large-pored side of a membrane, presuming sufficient hydrophilia, a rapid absorption of the sample and a liquid transport to the fine-pored side occur. Spreading out of the sample in the small pores preferentially occurs on the fine-pored side. The large pores are only filled very slowly, presuming sufficient sample volume. The flow resistance also increases with increasing fineness of the pores according to the Hagen-Poiseuille law, so that the transport speed is low in the case of very small pores in spite of high capillary activity. The transport through small pores is also slow over long distances, in the range of multiple millimeters. If a sample is delivered onto the fine-pored side of a membrane, spreading out of the sample occurs preferentially.

In the case of symmetrical membranes, spreading and penetration of on applied liquid sample into the membrane occurs uniformly. A preferential transport does not occur.

Real membranes are typically neither exactly symmetrical nor uniformly asymmetrical. A precise analysis of the structure and the transfer behavior is necessary for each membrane. Thus, for example, in membranes of the type MMM from Pall, Dreieich, Germany, it was observed that the largest pores are located approximately in the middle of the membrane thickness. This has the result that a liquid applied to the surface of the membrane spreads out preferentially and only penetrates the membrane thickness very slowly. In the case of small sample volumes, the sample does not reach the opposite side. Such membrane structures are not suitable for spreading layers.

Commercially available membranes, which allow a rapid passage of a liquid and a sufficiently rapid distribution, are asymmetrical and have pores having a mean pore size which is smaller than 1 μm on the fine-pored side. Asymmetrical membranes are described in WO 03/097219, Millipore Corporation, published Nov. 27, 2003; WO 98/25758, Memtec America Corporation, published Jun. 18, 1998; U.S. Pat. No. 6,110,369, Ditter et al., issued Aug. 29, 2000; EP 1 640 716, Arkray Inc., published Mar. 29, 2006; and EP 1 114 997, Arkray Inc., published Jul. 11, 2001.

If such a membrane is in close hydraulic contact with a porous, absorbent reagent layer, it has been recognized that hemolysis occurs in the case of blood as the sample liquid. The cause is suspected to be that erythrocytes are fixed in pores smaller than 3 μm to 4 μm and the capillary activity of the absorbent detection layer generates a sufficient differential pressure to cause the erythrocytes to burst. Membranes which separate the erythrocytes over their thickness so that hemolysis does not occur must have a very great thickness of approximately 300 μm, however, and require an excessively large blood volume. Their use as a spreading layer is therefore also precluded.

In the context of the invention, the term "mean pore size of a layer" is understood as the mean value of the pore size of the pores in the layer. Since this mean pore size typically may no longer be determined by measuring the individual pores, the mean pore size is defined so that the layer holds back 85% of particles having the size corresponding to the mean pore size. For example, if the mean pore size is 1 μm, 85% of all particles having a size of at least 1 μm are not let through by the layer.

Other known membranes, for example, those which are produced by peeling methods, as described in DE 2133848, Imperial Chemical Industries Ltd., published Jan. 20, 1972 (see also United Kingdom Publication No. 1331775, Imperial Chemical Industries Ltd., published Sep. 26, 1973) or in DE 10 2007 035 583, du Pont, published Apr. 17, 2008 (see also U.S. Pat. No. 7,964,049, Kapur et al., issued Jun. 21, 2011), for example, have a low permeability and a comparatively high thickness, which make them unsuitable for use as a spreading layer for blood analysis. In addition, they do not allow a targeted transport direction of a liquid sample.

In the context of the invention, it has been recognized that asymmetrical membranes could generally be suitable as a spreading layer, since they ensure a targeted transport direction of a sample. However, the known asymmetrical membranes do not have a suitable pore size. The membranes are implemented in such a manner that the mean pore size on one side is at least twice as large as the mean pore size on the opposite side of the membrane. The ratio of the mean pore size of one side of the membrane to the opposite side is preferably also greater, for example, 3 to 1, 5 to 1, 10 to 1, up to 100 to 1 or 200 to 1.

In the context of the invention, it has been recognized that a porous membrane, whose mean pore size at least sectionally increases over its thickness, is suitable for producing a spreading layer. A starting membrane is preferably used, which is an asymmetrical membrane in which the mean pore size of one side of the membrane increases toward the opposite side. A membrane in which the mean pore size increases continuously over the membrane thickness is particularly preferred. The method according to the invention for producing an analysis element spreading layer comprises the following steps:

A porous starting membrane having a bottom side and a top side and a starting thickness D between the bottom side and the top side is preferably supplied to a device for removing a sublayer. The starting membrane is implemented so that the mean size of the pores at least sectionally increases over its starting thickness. The side which has the larger pores and onto which the sample liquid are delivered during the use of the membrane as the spreading layer is designated hereafter as the top side. In a further method step, a sublayer of the starting membrane is removed at a predefined distance to its top side in that the starting membrane is cut parallel to the top side at the corresponding distance. Not only cutting or cutting through using a cutter or a blade is designated as "cutting", but rather also cutting using a rapidly moving tool, e.g., using a milling machine or a rotating milling machine. Alternatively, the starting membrane can also be cut using a laser beam or a water jet or similar means.

The second sublayer of the starting membrane remaining after the cutting of the first sublayer is the spreading layer. Its thickness d is less than the starting thickness D of the starting membrane. The pores of the spreading layer are in fluid connection to one another in such a manner that they are permeable to a liquid, so that a distribution of the liquid occurs on the liquid outlet side of the spreading layer. Of course, a liquid transport also occurs from the liquid inlet side to the liquid outlet side.

According to the invention, the spreading layer thus produced can be used to produce an analysis element for analyzing a liquid sample, which is distributed uniformly onto the analysis element. The analysis element has a test field and the above-described analysis element spreading layer. The test field (base element, test element) comprises a support layer and a test layer, which has at least one reaction layer (detection layer) having at least one reagent, which is part of the reagent system for the (optical) detection of an analyte in the liquid sample. The construction of such an incomplete test field, which is also designated as a test strip, is well known in the prior art. In particular, those test fields (base elements), in which the test layer is coated on the support layer in the form of a thin CTL, are suitable for producing the analysis element. These test fields lack a liquid retention structure, which is formed in the analysis element according to the invention by the produced spreading layer.

After the spreading layer has been supplied to the "incomplete" test element (test field), the spreading layer is applied to the still damp test field in such a manner that the liquid outlet side of the spreading layer presses against the top side of the test layer. The top side of the test layer is the side which is opposite to the support layer. The spreading layer is preferably curved in such a manner that it is "rolled" onto the test element. The spreading layer and the test field are connected to one another by the application, so that they jointly form the analysis element according to the invention.

Preferably at the point in time of the assembly, but at least at the point in time of the application of the spreading layer, a moisture film is formed on the top side of the test field, which has a thickness of at least a few micrometers. The spreading layer is held on the test field by this moisture film. The spreading layer is an asymmetrical membrane, which is already dried and which is preferably provided as a hydrophilic membrane or is hydrophilized.

In the case of this "lamination" of the spreading layer on the test field, it is important that the test layer is sufficiently moist. In a multilayer structure of the test field, the last, i.e., the uppermost layer must be moist, so that the top side of the test field (opposite to the support layer) is still moist. Moist in the meaning of the invention is understood as a relative moisture of at least 25% and at most 50%. Relative moisture designates the weight fraction of water in the test layer.

After the application of the spreading layer to the test field, the resulting analysis element is dried and an analysis element which is integral as a whole is formed. Surprisingly, the analysis element having the laminated membrane has improved properties after the drying in relation to the known analysis element having a typical spreading network. In particular, a lesser scattering of the measurement results is shown. A significantly lesser influence of the hematocrit on the test results is recorded in the assay of whole blood.

In the context of the invention, it has been recognized that, contrary to the expectations of persons skilled in the art, the suitability of such analysis elements for analyses of liquid samples, in particular of whole blood, is provided. It was feared that the kinetics of the reaction would be influenced by the laminated membrane. There were especially concerns in the technical world that enzymes or indicators from the test layer, in particular the reagent system, could be sucked into the membrane (spreading layer) during the production and in this way would make the analysis element unusable for the analysis. Furthermore, it was feared that, during the analysis, the enzymes and indicators sucked into the membrane would result in a reaction of a liquid which is not accessible to the optical evaluation and monitoring. It was expected that the signal deviation during the measurement would flatten out significantly and therefore the evaluation would be made more difficult. All of these concerns of the technical world have proven to be unfounded, however. Rather, the analysis element according to the invention is distinguished by improved measurement properties, in particular by lesser scattering of the results, and is especially suitable for the assay of small sample volumes in particular.

The membrane surface which is newly formed by the removal of the first sublayer of the starting membrane is the liquid outlet side of the spreading layer. The mean pore size on the liquid outlet side of the spreading layer is at least 1 μm. The mean pore size on the liquid outlet side is preferably at least 2 μm or at least 3 μm, particularly preferably at least 5 μm. Such a pore size ensures that no hemolysis occurs when blood is used as the body fluid sample.

The liquid outlet side of the spreading layer is distinguished in that it has a free pore area which is at least 70%, preferably at least 80%, and particularly preferably at least 90%. The spreading layer according to the invention therefore significantly differs from the previously known spreading layers.

In a preferred embodiment, a sublayer of the starting membrane is only removed on its bottom side, so that the top side of the starting membrane forms the top side of the spreading layer, which is the liquid inlet side. The side opposite to the top side forms the newly resulting membrane surface and is the liquid outlet side of the spreading layer.

A starting membrane is preferably used to perform the method according to the invention, whose mean pore size on the top side is at least 10 μm, preferably at least 20 μm, and particularly preferably at least 30 μm. In the context of the invention, it has been established that in a preferred embodiment, the starting membrane used has a mean pore size on the top side which is at most 60 μm, preferably at most 50 μm, particularly preferably at most 40 μm. Such a starting membrane is particularly suitable, since the top side of the starting membrane simultaneously forms the top side of the spreading layer and the pores on the liquid inlet side of the spreading layer are therefore correspondingly large.

Such a mean pore size on the top side, which forms the liquid inlet side of the spreading layer, has the advantage that upon contact of the spreading layer with a piercing element having capillary channel, by which the sample body fluid is absorbed in the case of a puncture in the skin, the sample liquid is suctioned by capillary forces with extremely high reliability from the capillary channel of the piercing element into the spreading layer. The capillary action of the pore size, which is significantly smaller in comparison to the capillary channel, ensures that the spreading layer absorbs the liquid.

The capillary action is increased by the pore size, which becomes smaller over the thickness of the spreading layer toward the liquid outlet side. It is thus ensured that the liquid entering the spreading layer is transferred to the liquid outlet side, which is adjoined by the test layer (test field) of the analysis element.

Therefore, the mean pore size on the liquid outlet side of the spreading layer is preferably at most 20 μm, more preferably at most 10 μm, particularly preferably at most 7 μm.

It has been established in the context of the invention that a strongly asymmetrical membrane is preferable as the starting membrane. The strongly asymmetrical membrane is distinguished in that the mean pore size increases strongly over its thickness, i.e., over its cross-section. The ratio of the mean pore size of the top side to the mean pore size of the bottom side is typically approximately 1:40 to 1:200, sometimes up to 1:1000.

The first sublayer is to be cut off of the starting membrane in such a manner that on the spreading layer formed, the liquid outlet side has a pore size of at most 20 µm, preferably at most 10 µm, particularly preferably at most 7 µm. In this manner, the "smallest pores" (smallest mean pore size) on the liquid outlet size of the spreading layer are sufficiently large that—under the application conditions of the analysis element and the optical analysis of blood—no hemolysis is caused. By cutting off the "fine-pored" sublayer, a spreading layer suitable for an optical analysis element for blood analysis results from an asymmetrical membrane, which is unsuitable per se. Furthermore, the spreading layer according to the invention is also applicable in analysis systems and analysis elements which electrochemically measure the quantity and/or the presence of an analyte.

In particular a starting membrane which comprises polyether sulfone (PESu) and is hydrophilized using hydroxypropyl cellulose is suitable for the cutting. For example, a membrane of the type BTS 25 from Pall, Dreieich, Germany is suitable as the starting membrane. Such a membrane has a "bubble point" of 25 PSI and a smallest mean pore size of nominally 0.45 µm. This nominal value is ascertained by filtration experiments. The membrane holds back 85% of particles having a diameter of 0.45 µm, i.e., 85% of all particles of this size are not let through by the membrane.

An asymmetrical starting membrane which is approximately 126 µm thick has the mentioned mean pore size of 0.45 µm on the top side and a pore size of 45 µm on the bottom side. After the cutting, a spreading layer having a thickness of 82 µm and an average pore size of 5.5 µm of the membrane surface formed by the cutting results. Such a membrane, in which the smallest mean pore size is 5.5 µm, is very well suitable for use as a spreading layer for optical blood analysis.

In an alternative method, a starting membrane of the type BTS 65 from Pall, Dreieich, Germany can be used. Such a membrane has a "bubble point" of 63 PSI and a smallest mean pore size of nominally 0.1 µm. Other membranes from the same product family, such as BTS 55, BTS 45, and BTS 25, can be used in a comparable way. The starting membrane is impregnated using a liquid such as water or a molten hydrophilic wax, such as PEG 1500, with the top side, the large-pored side, placed on an underlay, and cooled down enough that the impregnated liquid solidifies. The solidified liquid forms a friction-locked connection between the membrane and the underlay. The underlay is moved at a distance, which corresponds to the desired thickness of the spreading layer, under a cutting tool, e.g., a horizontally positioned solid cylindrical cutter. The solid cylindrical cutter removes the fine-pored sublayer. By supplying heat, the liquid is melted and flushed out using water in the case of PEG. After the drying, a membrane which can be used as a spreading layer is available. The membrane is preferably hydrophilic or is hydrophilized.

For continuous manufacturing, a starting membrane is preferably used as sheet material. For example, a roll or a roller, which has at least two temperature zones around its circumference, is used as the underlay. In the feed area of the membrane up to the position of the cutting tool, the underlay is at a temperature level below the melting point of the impregnating liquid. In the following area, the underlay is at a temperature level above the melting point of the impregnating liquid. A fixed blade, a horizontally vibrating blade, a solid cylindrical cutter, or another suitable machining tool is used as the cutting tool. The membrane is impregnated with the impregnating liquid, if necessary at elevated temperature, before feeding to the roller. Excess impregnating liquid is stripped off using means known in the prior art. The impregnated membrane is rolled on to the (rotating) roller and freezes on. The undesired sublayer is removed. As the rotation of the roller continues, thermal energy is supplied by thermal radiation, hot air, or hot water, for example, and the impregnating liquid melts. The remaining membrane is drawn off of the roller, washed using water in a next station if necessary, and flushed free of the impregnating liquid. In a further station, the water is removed by drying and the product, the spreading layer, can be wound onto a roll or processed further.

For example, the spreading layer can be used to produce an optical analysis element. The dry spreading layer is then supplied to a test field having a transparent support layer and a test layer and is laminated onto the top side of the test layer, which faces away from the support layer. The spreading layer and the test field are permanently connected to one another by the lamination and jointly form the analysis element.

DRAWINGS

The invention is explained in greater detail hereafter on the basis of specific embodiments which are shown in the figures. The special features shown therein can be used individually or in combination to provide preferred embodiments of the invention. The proportions shown of the individual components sometimes do not correspond to illustrate details. The described embodiments do not represent a restriction of the generality of the invention defined by the claims.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
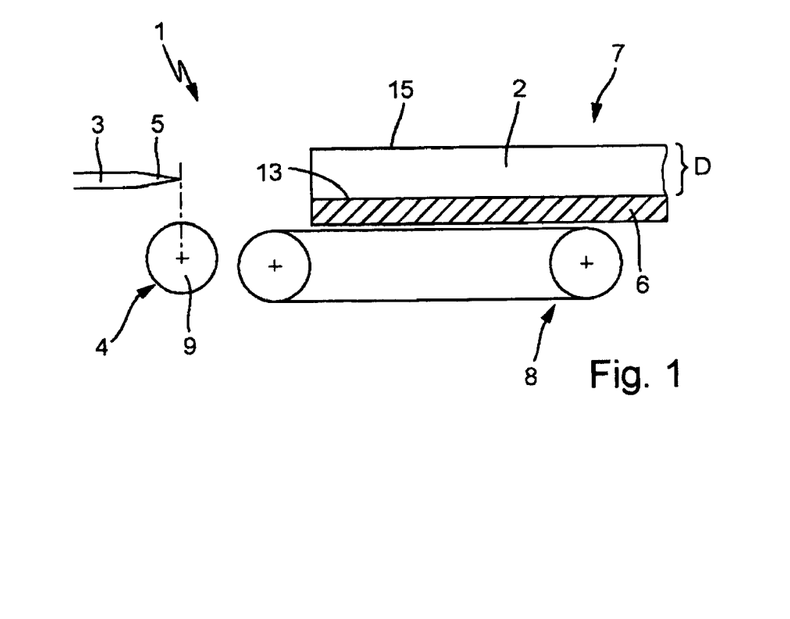
FIG. 1 shows a schematic diagram of a cutting device for removing a sublayer of a starting membrane.

FIG. 1 shows a cutting device 1, using which a starting membrane 2 can be divided into two sublayers in such a manner that a spreading layer according to the invention is produced. The cutting device 1 includes a cutting blade 3 having a sharp edge 5. The cutting blade 3 can be implemented like a razor blade or similarly to a scalpel, for example.

The cutting device 1 preferably also comprises a deflection device 4, by which the starting membrane 2 is redirected during the production process. The starting membrane 2 is cut by the cutting device 1 upon passing the deflection device 4. In a preferred embodiment, the deflection device 4 is implemented as a roller 9, as shown in FIG. 1, which is preferably rotatable.

In order to supply the starting membrane 2 to the cutting blade 3, for example, a conveyor belt 8 can be used, which is positioned in such a manner that the top side of the conveyor belt 8 runs tangentially to the roller 9. In a preferred embodiment, the deflection device 4 can have a fixed edge, on which the starting membrane 2 is deflected, as an alternative to the rotatable roller 9. The fixed edge is preferably rounded. The edge fulfills the function of the roller 9 and is positioned so that the starting membrane is cut upon passing the edge.

FIG. 1 shows that the starting membrane 2 is fastened on an underlay 6 and forms a material web 7, which is moved toward the coupling device 1, jointly with the underlay 6. The underlay 6 used as a carrier can be an adhesive strip or an adhesive tape, for example. It is also possible to provide an adhesive layer between the underlay 6 and the starting membrane 2. The starting membrane 2 is preferably glued with its bottom side 13 onto the underlay 6. The material web 7 is positioned on the conveyor belt 8 in such a manner that the underlay 6 rests on the conveyor belt 8 and comes in contact with the roller 9 upon passing it. When a sublayer is cut off of the starting membrane 2, which is preferably at least 80 μm, particularly preferably at least 120 μm thick, the top sublayer is removed from the bottom sublayer having the underlay 6. The top sublayer is than the desired spreading layer, whose thickness d is at least 30 μm, preferably at least 50 m, and particularly preferably at least 70 μm.

Figure 2:
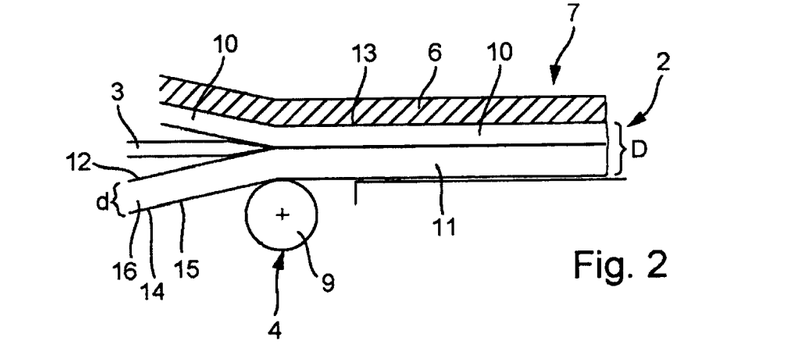
FIG. 2 shows a schematic diagram of the removal of a sublayer of the starting membrane using a cutting device.

FIG. 2 shows a detail view of the cutting device 1 from FIG. 1, but without a conveyor belt. Instead of the conveyor belt, a flat plate is provided, via which the material web 7 having the porous starting membrane 2 is manually supplied to the cutting device 1.

In a preferred embodiment of the production method, the top side 15 of the starting membrane 2 is moved over the deflection device 4. The fine-pored top side 13 of the starting membrane 2 is preferably fastened on the underlay 6. During the supply of the starting membrane 2 to the cutting blade 5, the underlay 6 is oriented upward, while the bottom side 15 comes into contact with the roller 9. Through such an arrangement of the starting membrane 2, thickness variations of the adhesive tape or the adhesive layer between starting membrane 2 and underlay 6 can be eliminated.

Preferably, the position of the cutting blade 3 and its edge 5 is fixed (preferably parallel) to the deflection device 4. In particular, the distance between the edge 5 and the surface of the roller 9 is constant. An eccentricity of the roller is compensated for by the coupling of the edge 5 of the cutting blade 3 to the roller 9. Since the top side 15 of the membrane 2, and therefore the sublayer 11 of the membrane 2 which will form the spreading layer 16 after the cutting, is moved via the roller 9, the coupling results in a very high precision of the thickness of the spreading layer 16 to be produced.

The edge 5 is movable transversely to the movement direction of the starting membrane 2 and parallel to the rotational axis of the roller 9. It vibrates in the movement plane of the starting membrane 2. A rapid vibration of the edge 5 is preferred, for example, using ultrasound. These transverse vibrations are such that the distance of the edge 5 to the surface of the roller 9 always remains constant. A very exact cut is made possible by the moving edge 5.

In the context of the invention, it was established that the cutting quality and the quality of the generated membrane surface of the spreading layer can be significantly improved by moistening the starting membrane with water or another material acting as a lubricant. The cutting resistance of the moistened membrane is significantly reduced. The moistening of the porous starting membrane can be performed before or during the removal of the one sublayer of the starting membrane 2. The membrane is to be moist at least during the cutting.

Alternatively, the pore structure of the starting membrane 2 can also be filled using liquids which are brought to a temperature below the melting point of the liquid before the cutting off of the sublayer. In addition to water, waxes are suitable, preferably water-soluble waxes from the family of polyethylene oxides. They are dissolved from the pores again after the cutting and cutting off of the spreading layer. This can be performed in a washing process at corresponding temperatures, for example. Subsequently, the spreading layer can be dried and wound up. Alternatively, of course, it is also possible to fasten, for example, to laminate the spreading layer on a test layer of an analysis element directly after the drying. It is therefore possible to join a carrier material coated with a test layer with the spreading layer by lamination, in order to form an analysis element.

During the cutting procedure of FIG. 2, the starting membrane 2, which is glued with its bottom side 13 on the underlay 6, is cut in such a manner that a first sublayer 10 having the fine-pored pores, whose pore size is too small for the function of a spreading layer, is separated and moved away over the edge 5. The second sublayer 11 is guided along between the edge 5 and the roller 9. It has the precise, desired thickness d, preferably of approximately 40 μm to approximately 100 μm, and forms the spreading layer 16. The newly formed membrane surface of the spreading layer 16 is the liquid outlet side 12 of the spreading layer 16. The top side 15 of the starting membrane 2 forms the top side of the spreading layer 16, which is the liquid inlet side 14.

Figure 3:
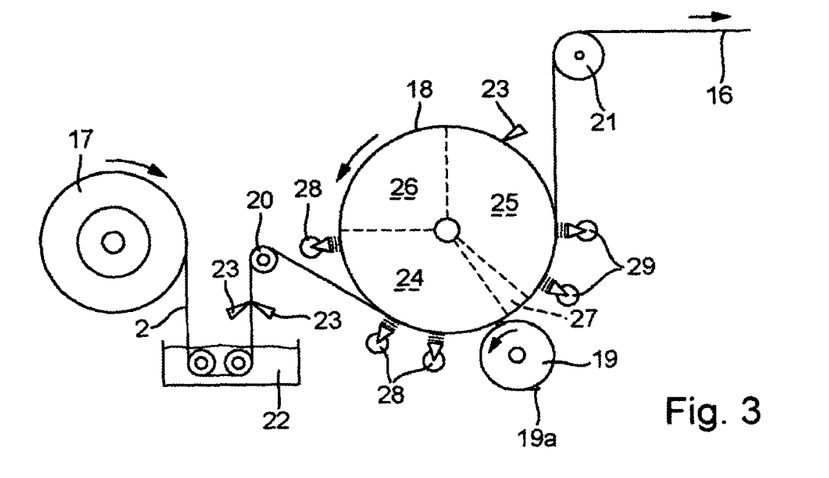
FIG. 3 shows a schematic diagram of an alternative cutting device.

An alternative cutting device 1 is shown in FIG. 3. In this embodiment, the starting membrane 2 is provided as sheet material and is unwound from a starting membrane roll 17. The starting membrane 2 is guided through an impregnation station 22, in which it is impregnated using an impregnating liquid, for example, water or molten wax.

Excess impregnating liquid is stripped off on a stripper 23, which is positioned behind the impregnation station 22 in the movement direction. The starting membrane sheet material is redirected on a first redirection roll 20 and guided to a roller 18, which preferably has a diameter of at least 30 cm. The roller 18 is part of a deflection device 4.

The sheet material is moved through between the roller 18 and a solid cylindrical cutter 19 in such a manner that a first sublayer 10 is removed from the starting membrane sheet material and the desired spreading layer 16 results. The spreading layer 16, which now forms the sheet material, is guided over a further deflection roll 21, before it is wound up on a roll and/or processed further, for example.

The roller 18 is cooled down by at least one cold air nozzle 28 in a first area (cooling sector 24). In the preferred embodiment according to FIG. 3, three cold air nozzles 28 are provided. The cold air nozzles 28 are positioned in such a manner that it is cooled down in the intake area of the membrane up to the position of a cutting tool implemented as the solid cylindrical cutter 19. The cooling is performed to a temperature level below the melting point of the impregnating liquid used, i.e., below the freezing point in the case of water, in such a manner that the starting membrane 2 freezes onto the roller 18 in the cooling sector 24 and is fixed to it. The movement speed of the starting membrane 2 therefore corresponds to the roller speed. Shear forces are transferred from the starting membrane 2 to the roller 18.

The solid cylindrical cutter 19 preferably has a plurality of small blades 19a, only two of which are shown in FIG. 3 for reasons of clarity. A first sublayer 10 is cut off of the starting membrane 2 with the aid of the solid cylindrical cutter 19, so that the desired spreading layer 16 remains as the sheet material. The web-shaped spreading layer 16 is moved further using the roller 18 to an area (heating sector 25), in which a plurality of, for example, two hot air nozzles 29 are positioned. The supplied thermal energy, which can be in the form of hot air or thermal radiation, for example, heats the impregnated spreading layer 6 in such a manner that the impregnating liquid melts and liquefies, so that the spreading layer 16 can be removed from the roller 18.

A further stripper 23 is provided on the roller 18, to remove excessive impregnating liquid in the heated area (heating sector 25) from the roller 18, in which the roller surface has an elevated temperature, which is above the melting point of the impregnating liquid. Excess residues are removed in this manner, so that the very precise and smooth surface of the roller 18 is maintained.

FIG. 3 shows that the roller 18 has four sectors, the cooling sector 24, the heating sector 25, which has an elevated surface temperature, and two neutral sectors 26, 27, which are positioned between the cooling sector 24 and the heating sector 25. In these areas 26, 27, the surface of the roller 18 has a temperature which is between the temperatures in the respective adjacent sectors 24 and 25 in an uncontrolled manner.

Figure 4:
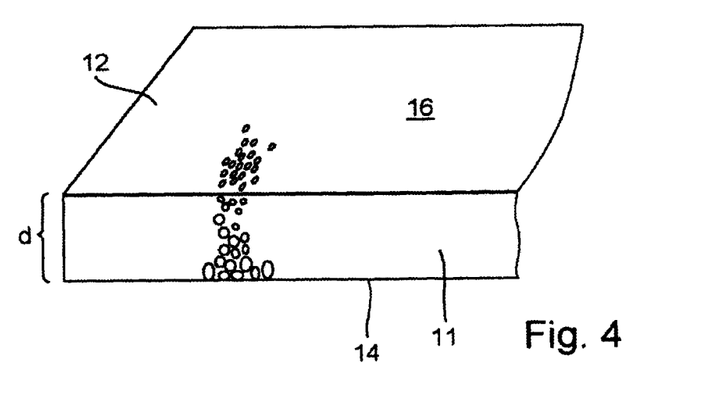
FIG. 4 shows a spreading layer produced from a starting membrane.

FIG. 4 shows an example of a spreading layer 16 for an optical analysis element produced using the method according to the invention. The spreading layer 16 is suitable for absorbing a body fluid to be analyzed and for uniformly distributing the liquid over its liquid outlet side 12.

The spreading layer 16 is formed from a porous membrane and corresponds to the cut-off sublayer 11 of the membrane 2. The spreading layer 16 has a liquid inlet side 14, which is formed from the top side 15 of the starting membrane 2, opposite to the liquid outlet side 12. The thickness d is at least 40 μm, preferably at least 60 μm, and particularly preferably at least 80 μm and is therefore less than the starting thickness D of the membrane 2.

The pores of the spreading layer 16 have a fluid connection to one another in such a manner that they are permeable to a liquid and transport a liquid entering on the liquid inlet side 14 to the liquid outlet side 12 and distribute it over the liquid outlet side 12. The mean pore size of the spreading layer 16 increases along its thickness d in such a manner that the mean pore size on the liquid inlet side 14 is greater than that on the liquid outlet side 12. The increase of the mean pore size is preferably continuous over the thickness d, i.e., over the cross-section of the spreading layer 16. The mean pore size on the liquid outlet side 12 is at least 1 μm, preferably at least 2 μm, and particularly preferably at least 5 μm. The mean pore size on the liquid outlet side 12 is at most 20 μm, preferably at most 10 μm, particularly preferably at most 7 μm.

On its membrane surface newly formed by the cutting process, which is the liquid outlet side 12, the spreading layer 16 has a free pore area which is at least 70% or 75%, preferably at least 80% or 85%, and particularly preferably at least 90% or 95%. The free pore area on the newly formed liquid outlet side 12 is therefore greater than the free pore area on the bottom side 13 of the starting membrane 2. It is preferably at least twice as large, particularly preferably at least five times as large. The free pore area of the liquid outlet size 12 is also larger, preferably at least twice as large, in comparison to a bottom side of a membrane which is produced in a typical production process and has the same mean pore size. The spreading layer 16 produced by cutting therefore differs from a membrane which results through the known production processes such as peeling, etching, sintering, or phase inversion.

Figure 5A:
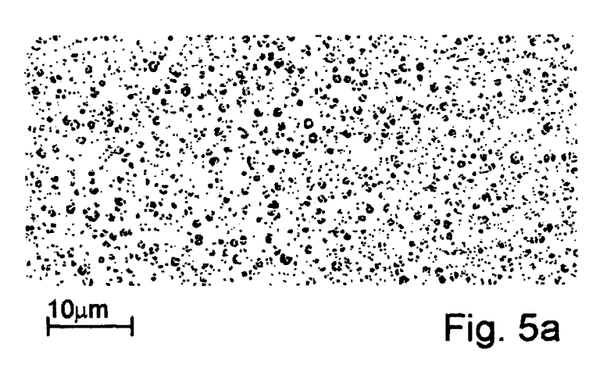
FIGS. 5a and 5b show a membrane surface of a membrane.

FIG. 5a shows a scanning electron microscope image of the bottom side of a starting membrane BTS 65. The free pore area, i.e., the relative open area (total opening area of the pores in relation to the total area) is only small and is less than 30%.

Figure 5B:
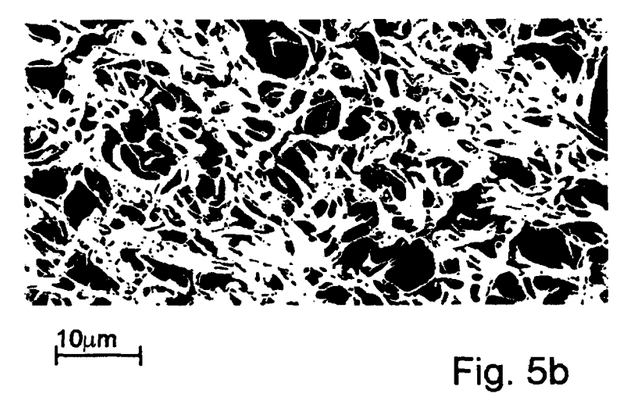

FIG. 5b shows a scanning electron microscope image of the membrane surface of a spreading layer which was obtained by machining removal of a sublayer after impregnation with PEG 1500, as described above. The enlargement scale of the image is identical to the enlargement scale of the image in FIG. 5a. The free pore area is significantly enlarged. The ratio of all pore openings to the total area is greater than 75%.

Figure 6:
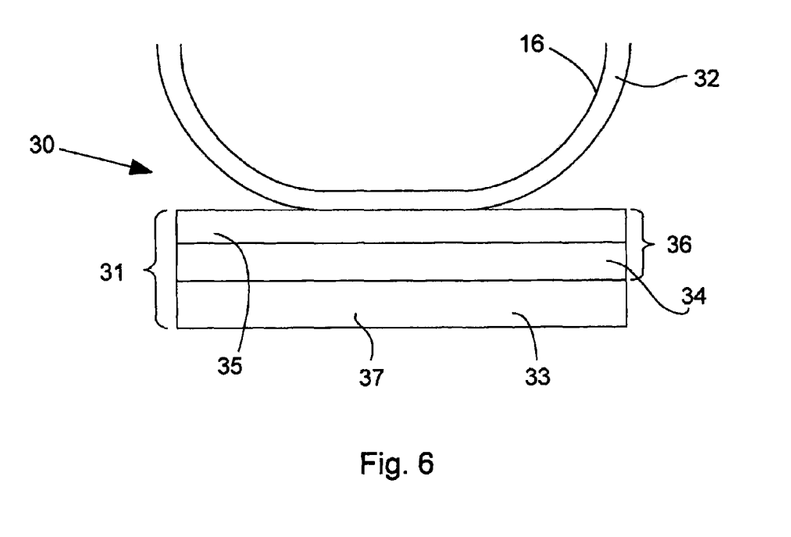
FIG. 6 shows a schematic diagram of the production of an analysis element.

FIG. 6 shows a schematic view of the production of an analysis element 30 according to the invention, which comprises a test field 31 and the spreading layer 16 according to the invention, which is provided in the form of a dried, hydrophilic membrane 32. The test field 31 has a carrier film 33, which forms the support layer 37 of the analysis element 30. A reaction layer 34 (detection layer), which contains at least one reagent of a reagent system to detect an analyte, is applied to the transparent carrier film 33. In the case of an optical analysis element 30, a reflection layer 35 (e.g., made of zinc oxide or titanium oxide) is positioned above the reaction layer 34. The reaction layer 34 and the reflection layer 35 form a test layer 36.

It can be inferred from FIG. 6 that in the production process of the analysis element 30, the spreading layer 16 (membrane 32) is laminated onto the dried but still moist reflection layer 35 of the test layer 36, i.e., brought into contact therewith. In the case of a multilayer system, the membrane 32 is laminated onto the top (last) layer of the test field. The spreading layer 16 was obtained by removing a sublayer of a porous starting membrane 2, as described above, at a predefined distance to the top side 15 of the starting membrane 2. The spreading layer 16 was preferably produced by cutting parallel to the top side 15.

It has proven to be advantageous in laboratory experiments to lay the membrane 32 curved in loop form slowly onto the still moist test layer 36, so that it is rolled onto the test layer 36. The membrane 32 suctions onto the moist test layer 36. A liquid film is preferably formed on the top side of the test field 31. The existing liquid (moisture) initially assumes the function of an adhesive, which fixes the membrane 32 on the test field 31. After the drying, a solid composite, which can be processed well, made of test field 31 and spreading layer 16 (membrane 32) results. In the dry state, the polymer contents of the test field, in particular the reflection layer 35, ensure binding of the membrane 32.

Figure 7:
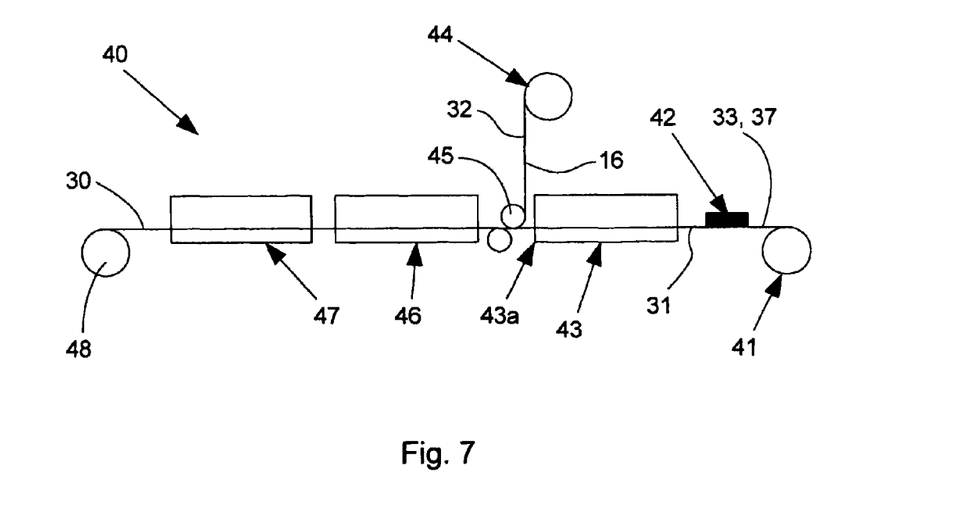
FIG. 7 shows a schematic diagram of a production plant for producing an analysis element.

FIG. 7 shows a production plant 40, in which the carrier layer 37 is implemented as a band-shaped carrier film 33 and wound onto a carrier roll 41. The carrier film 33 is unwound from this carrier roll 41 and passes through a coating unit 42, in which the carrier film 33 is coated with the test layer 36 (reaction layer 34 and reflection layer 35). In a first dryer unit 43, the test field 31 now resulting is dried, wherein it still contains the desired moisture at the end 43a of the dryer unit 43.

The spreading layer 16 according to the invention, which is wound as a web-shaped membrane 32 onto a membrane roll 44, is supplied via a redirection roll 45 to the band-shaped test field 31. The membrane 32, as described on the basis of FIG. 6, is laid on the test field 31 and suctions fixedly thereon. Lamination of the membrane is thus implemented.

It is decisive in the production facility 40 that the test layer 36 is neither excessively dry nor excessively wet. The test layer 36 is advantageously moist in a manner corresponding to the state after approximately 3 to 11 min. drying time at room temperature. The test element 36 preferably has a moisture between 30% and 50%. It has proven to be advantageous if the relative moisture during the lamination is between 35% and 47%. A relative moisture of 40% to 45% is particularly preferred.

After the lamination of the membrane 32 onto the test field 31, the resulting composite element, which is the band-shaped analysis element 30, is dried in two further drying units 46 and 47 until the analysis element band is wound onto a composite roll 48. The analysis element 30 is then available for further processing.

Figure 8A:
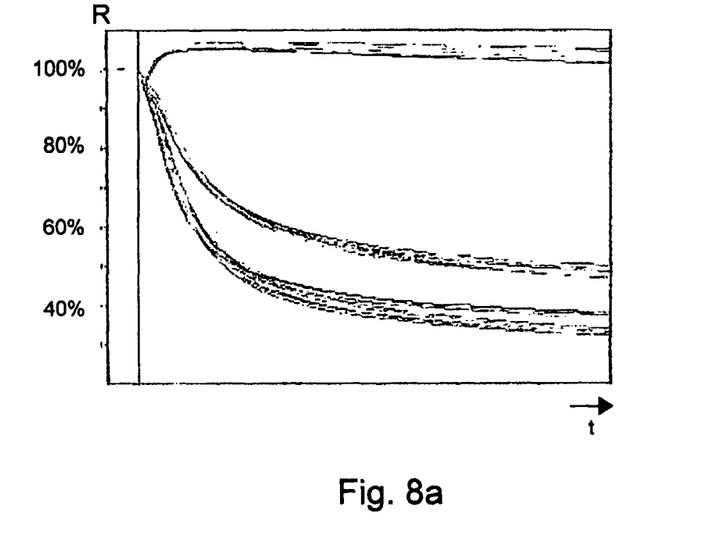
FIGS. 8a and 8b show the time curve of whole blood measurements having different glucose contents on two analysis elements.
Figure 8B:
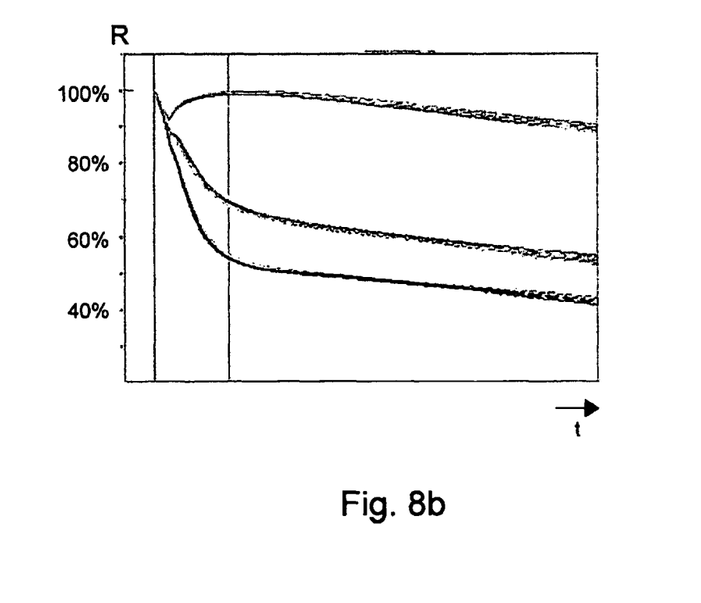

The "kinetic curves" in FIGS. 8a and 8b show the time curve of the measurement on different analysis elements. The relative remission R of the received light is measured. Therefore, the measured variable is the reflected light, which is set in relation to a blank measurement (reference measurement), in which no liquid wets the reaction layer 34 of an analysis element 30. FIGS. 8a and 8b each show three curve families of multiple measurement series using whole blood with different glucose contents. The top curve family (measurement series) shows the result of whole blood having a glucose content of 0 mg/dl, while the measurements of the middle curve family were performed using a glucose content of 250 mg/dl and the measurements of the bottom curve family were performed using a glucose content of 545 mg/dl in whole blood.

In FIG. 8a, the measurement results of a typical analysis element, which uses a monofilament fabric as the spreading layer 16, are shown. The monofilament fabric is applied to a test field. FIG. 8b shows the measurement results when an analysis element 30 according to the invention having laminated membrane 32 is used. The comparison of both FIGS. 8a and 8b shows that if the analysis element 30 according to the invention is used, a significantly smaller scattering is to be reported within the respective curve family. The measurement results provide an indication that the analysis element 30 has improved test properties and measurements are significantly more reliable and informative.

Figure 9A:
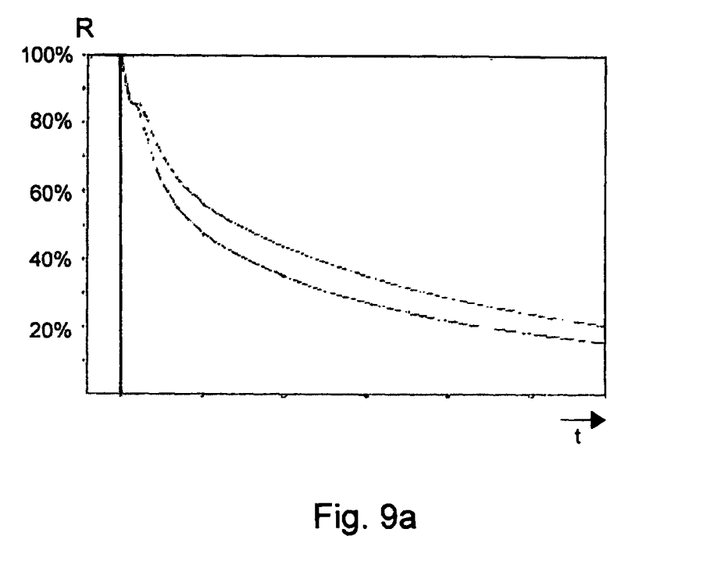
FIGS. 9a and 9b show the time curve of whole blood measurements having different hematocrit values on two analysis elements.
Figure 9B:
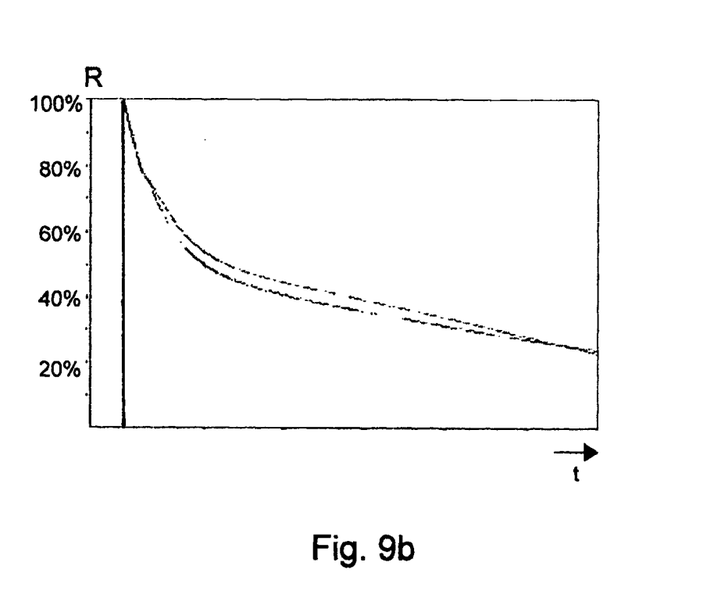

FIGS. 9a and 9b each again show the comparison of the two analysis elements (having monofilament fabric and spreading layer 16 according to the invention). In each case, the mean value of the remission R of 12 measurement series is shown, wherein the sample liquid comprised whole blood having 250 mg/dl glucose fraction. The hematocrit value is 40% (top curve), 45% (middle curve), and 50% (bottom curve). The comparison of both FIGS. 9a and 9b shows that if the analysis element 30 according to the invention having spreading layer 16 according to the invention is used (FIG. 9b), a significantly lower influence of the hematocrit is to be reported, since the three curves are significantly closer to one another.

In summary, it may be stated that, using the analysis elements 30 according to the invention, in comparison to test strips or analysis elements having a typical spreading network made of monofilament fabric, a significantly reduced scattering of the measurement results and a significantly reduced influence of the hematocrit on the results are recorded. Therefore, the effects feared by the technical world of experts do not occur, that the enzyme or the indicator would be sucked out of the reagent system into the membrane 32 and the signal deflection would flatten and more difficult evaluation of the results would be possible. In contrast, it has been shown that the analysis element according to the invention is significantly better suitable.

In addition, the use of the spreading layer 16 according to the invention in the form of a membrane 32, which is laminated on to the test field 31, has the advantage, if band-shaped analysis elements 32 or test strips are used, that a correct result is also achieved in the case of small sample volumes. In the event of a tension on the band-shaped analysis element 30, raising of the spreading layer 16 off of the test layer 36 of the test field 31 also does not occur due to the process of the lamination, as can occur if monofilament spreading networks are used. A more reliable production process may thus be implemented.

What is claimed is:

1. A method for producing an analysis element spreading layer, which is implemented for absorbing a liquid to be analyzed in an analysis element and distributing it uniformly over a liquid outlet side of the analysis element spreading layer, the method comprising the following steps:
   supplying a porous starting membrane having a top side, a bottom side and a starting thickness D between the bottom side and the top side, the size of the pores of the starting membrane increasing at least sectionally over its starting thickness D,
   selecting a predefined distance within the starting thickness D of the starting membrane parallel to the top side of the starting membrane corresponding with a desired mean pore size;
   cutting the starting membrane at the predefined distance in such a manner that a sublayer of the starting membrane is removed, wherein
      the analysis element spreading layer is a sublayer of the starting membrane, having a thickness d that is less than the starting thickness D of the starting membrane,
      the pores of the analysis element spreading layer are in fluid connection to one another in such a manner that the analysis element spreading layer is permeable to a liquid,
      the membrane surface formed by the removal of a sublayer of the starting membrane is the liquid outlet side of the analysis element spreading layer, and
      the mean pore size of the pores on the liquid outlet side of the analysis element spreading layer is at least 1μm and
   supplying the analysis element spreading layer formed to a test field having a reaction layer with at least one reagent, which is part of a reagent system for detecting an analyte in the liquid sample.

2. The method according to claim 1, wherein a sublayer is only removed on the bottom side of the starting membrane, so that the top side of the starting membrane also forms a top side of the spreading layer, the side opposite to the top side being the liquid outlet side of the spreading layer.

3. The method according to claim 1, wherein the starting membrane is fastened on an underlay and is moved jointly with the underlay as a material web to a cutting device, by means of which the starting membrane is cut.

4. The method according to claim 1, wherein cutting the starting membrane comprises supplying a cutting device that comprises a deflection device, by which a material web containing the starting membrane is deflected during the production process, the starting membrane being cut upon passing the deflection device.

5. The method according to claim 4, wherein the top side of the starting membrane is moved over the deflection device.

6. The method according to claim 1, wherein the starting membrane, before the removal or during the removal of a sublayer, is impregnated with a liquid, preferably with water, an aqueous solution, or a molten water-soluble wax.

7. The method according to claim 6, wherein the cutting device comprises a roller, and that the starting membrane impregnated with liquid will be frozen on a section of the roller in such a manner that, during the cutting, the starting membrane is frozen on the section of the roller and is moved with the roller.

8. The method according to claim 1, wherein the starting membrane comprises an asymmetrical membrane.

9. The method according to claim 1, wherein the mean pore size on the liquid outlet side of the spreading layer is at least 2 μm.

10. The method according to claim 9, wherein the mean pore size on the liquid outlet side of the spreading layer is at most 20 μm.

11. The method according to claim 1, wherein the mean pore size on the top side is at least 10 μm.

12. The method according to claim 11, wherein the mean pore size on the top side is at most 60 μm.

13. The method according to claim 1, wherein the free pore area on the liquid outlet side of the spreading layer is at least 70%.

14. A spreading layer of an analysis element for absorbing a liquid to be analyzed and for uniformly distributing the liquid over a liquid outlet side, by a method according to claim 1, wherein
- the spreading layer is a porous membrane, which has a top side opposite to the liquid outlet side, which forms a liquid inlet side;
- the spreading layer comprises a plurality of pores, which are in fluid contact with one another in such a manner that the spreading layer is permeable to a liquid;
- the mean pore size increases along the thickness d of the spreading layer in such a manner that the mean pore size on the liquid inlet side is greater than the mean pore size on the liquid outlet side;
- the mean pore size on the liquid outlet side is at least 1 μm; and
- the free pore area on the liquid outlet side of the spreading layer is at least 70%.

15. A method for producing an analysis element for analyzing a liquid sample, which comprises a test element and an analysis element spreading layer, comprising the following steps:
- supplying a porous starting membrane having a top side, a bottom side, and a starting thickness D between the bottom side and the top side, the size of the pores of the starting membrane at least sectionally increasing over its starting thickness D,
- selecting a predefined distance within the starting thickness D of the starting membrane parallel to the top side of the starting membrane corresponding with a desired mean pore size;
- removing a sublayer of the starting membrane at the predefined distance parallel to the top side in such a manner that the analysis element spreading layer is a sublayer of the starting membrane having a thickness d, which is less than the starting thickness D of the starting membrane, wherein
  - the pores of the analysis element spreading layer are in fluid connection to one another in such a manner that the analysis element spreading layer is permeable to a liquid,
  - the membrane surface formed by the removal of a sublayer of the starting membrane is the liquid outlet side of the analysis element spreading layer, and
  - the mean pore size of the pores on the liquid outlet side of the analysis element spreading layer is at least 1 μm,
- supplying the analysis element spreading layer formed to a test field having a support layer and a test layer, wherein the test layer comprising a reaction layer having at least one reagent, which is part of a reagent system for detecting an analyte in the liquid sample,
- applying the analysis element spreading layer to the test field in such a manner that the liquid outlet side of the analysis element spreading layer presses against a top side of the test layer, so that the analysis element spreading layer and the test field are connected and jointly form the analysis element.

16. The method according to claim 1, wherein the analysis element spreading layer is provided as a hydrophilic membrane or is hydrophilized.

* * * * *